United States Patent [19]

Simpson

[11] 4,273,130

[45] Jun. 16, 1981

[54] CONSTRICTOR

[76] Inventor: Judith V. Simpson, 307 MacLaren La., Lake Bluff, Ill. 60044

[21] Appl. No.: 968,173

[22] Filed: Dec. 11, 1978

[51] Int. Cl.³ ............................................. A61B 17/12
[52] U.S. Cl. .................................. 128/327; 128/134; 128/DIG. 15; 2/DIG. 6; 2/338; 273/189 A; 24/204
[58] Field of Search ....... 128/327, 133, 134, DIG. 15, 128/326, 169, 165, 157, 78, 87 R; 2/DIG. 6, DIG. 11, 338; 273/189 A, 189 R; 24/31 V, 68 SK, 71 SK, 204

[56] References Cited

U.S. PATENT DOCUMENTS

| | | | |
|---|---|---|---|
| 1,473,041 | 11/1923 | Henderson | 128/327 |
| 1,880,908 | 10/1932 | Duffy, Jr. | 2/338 |
| 3,000,384 | 9/1961 | Piers, Jr. | 128/DIG. 15 |
| 3,086,529 | 4/1963 | Munz et al. | 2/DIG. 6 |
| 3,426,363 | 2/1969 | Girard | 2/338 |
| 3,561,436 | 2/1971 | Gaylord, Jr. | 128/157 X |
| 3,586,001 | 6/1971 | Sanderson | 128/327 |
| 3,930,506 | 1/1976 | Overend | 128/327 |
| 3,942,525 | 3/1976 | Dragan | 128/DIG. 15 |
| 4,149,540 | 4/1979 | Hasslinger | 128/327 |
| 4,182,338 | 1/1980 | Stanulis | 128/327 |

OTHER PUBLICATIONS

"Velcro Industrial D-Rings are used as Cinching Belts in all Types of Industry Where Accessibility To Tubes, Ducts or Pipes is Required", 1962.

Primary Examiner—Henry J. Recla
Attorney, Agent, or Firm—Thomas W. Speckman

[57] ABSTRACT

A constrictor of an elongated flexible strip having a ring affixed to one end and an end tab at the other end wherein the strip has an elastic portion and a first and second coupling surface portion on the same face of the strip, the coupling surfaces upon contact cooperating to provide resistance to slidable motion and easy disengagement by separation of the surfaces.

10 Claims, 7 Drawing Figures

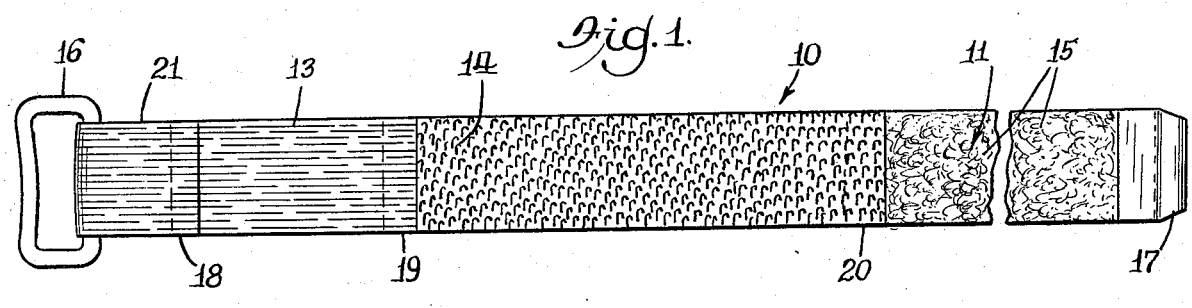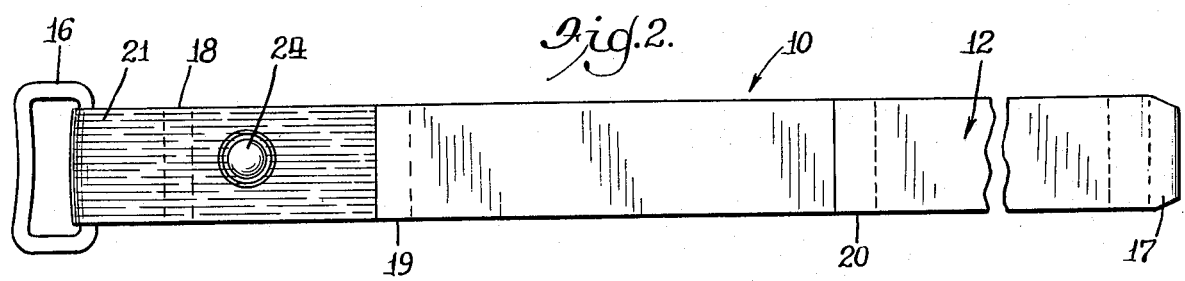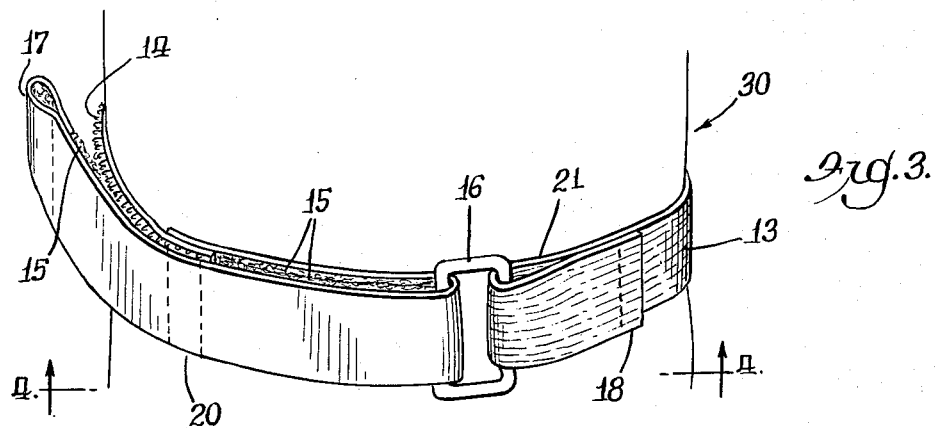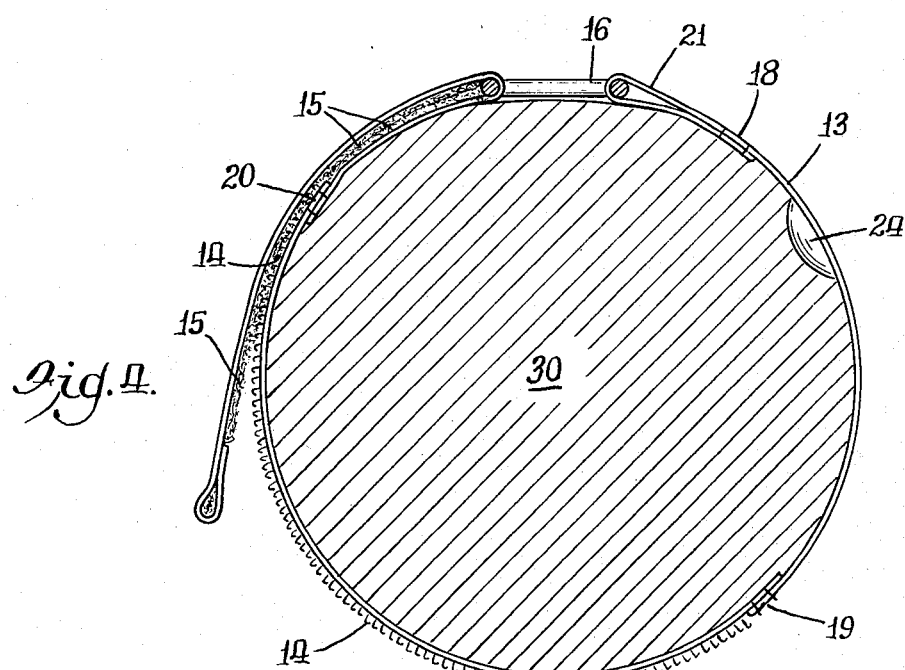

CONSTRICTOR

This invention relates to a constrictor of the type frequently used in medical practice for effecting constriction of limbs.

A number of different types of constrictors have been used for constricting a limb of the body to control circulation of blood. Frequently, small diameter rubber tubing is wrapped around the limb and while being stretched the ends are tied into an easily released knot. This method requires the use of two hands, is cumbersome and frequently results in undesirable pinching of the skin or flesh by the knot. Another type of constrictor to avoid tying of knots in rubber tubing is a strip of flexible material which is wrapped around the limb to be constructed so that it overlaps itself in the same direction with projections from one portion of the strip extending through openings in an adjacent layer of the strip preventing movement. Constrictors of this type are more fully described in U.S. Pat. No. 2,519,712. An improvement of the overlapping type of constrictor is taught by U.S. Pat. No. 3,086,529 wherein Velcro is attached to opposite ends and on opposite faces of an elastic strip. However, the constrictor taught by the U.S. Pat. No. 3,086,529 patent still requires two hands for its application and does not allow easy adjustment.

It is an object of this invention to overcome many of the disadvantages of prior art constrictors.

It is still another object of this invention to provide an elastic constrictor which may be readily applied with one hand.

It is yet another object of this invention to provide a constrictor which may be simply adjusted using one hand.

It is still another object of this invention to provide a restrictor which does not pinch nor bruise a limb around which it is applied.

It is another object of this invention to provide a constrictor which in a single size permits use on a wide range of limbs of different size.

It is still another object of this invention to provide a constrictor which may be quickly and controllably released.

It is another object of this invention to provide a constrictor having a localized pressure applicator.

It is yet another object of this invention to provide an inexpensive disposable constrictor.

It is still another object of this invention to provide a constrictor which is suitable for use as an elastic binding and holder for wound dressings.

These and other objects of the invention become apparent upon reading the following description and by reference to the drawings showing preferred embodiments wherein:

FIG. 1 shows one face of a constrictor according to a preferred embodiment of this invention;

FIG. 2 shows the opposite face of the constrictor shown in FIG. 1;

FIG. 3 shows a constrictor according to one embodiment of this invention as shown in FIGS. 1 and 2 applied around a limb;

FIG. 4 shows a sectional view as indicated as 4—4 in FIG. 3 with a localized pressure applicator;

Figure 5:
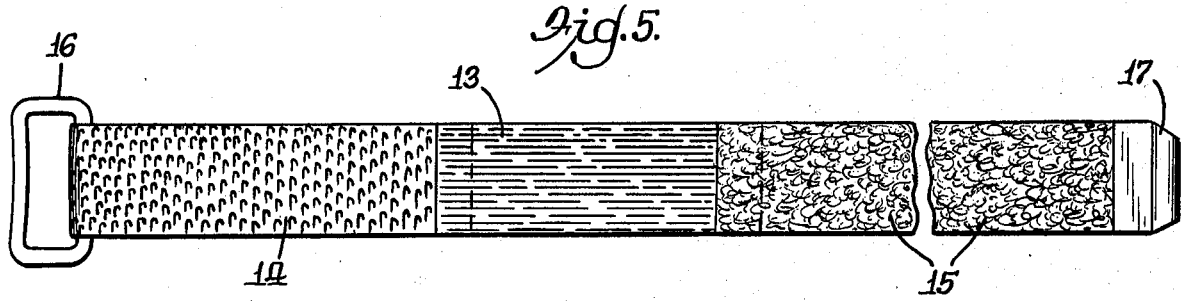
FIG. 5 shows one face of a constrictor according to another embodiment of this invention.

Referring to the figures, particularly FIG. 1 and FIG. 2, constrictor 10 is shown as an elongated flexible strip having ring 16 affixed to one end and end tab 17 at the other end. The elongated flexible strip consists of elastic portion 13 shown as elastic fabric, first coupling surface portion 14 and second coupling surface portion 15, both coupling surface portions being on the same face 11 of the elastic strip. The first and second coupling surfaces cooperate upon contact to provide a fixed relation between the surfaces which is readily releasable by separation of the surfaces. The elastic portion may be any suitable flexible strip such as elastic fabric or moled plastic having an embossed design providing elastic properites. The remainder of the flexible strip may be any natural or synthetic fabric or plastic providing desired flexibility.

The coupling surfaces may be any suitably engaging surfaces which upon contact provide resistance to slidable motion between the two surfaces while providing disengagement by pulling the surfaces away from each other. Suitable surfaces may be provided wherein one coupling surface has a multiplicity of outwardly projecting loops of filamentary material and the other coupling surface has a multiplicity of curly filamentary members releasably engageable with the projecting loops. One suitable commercially available material for use as the coupling surfaces, one of which has projecting loops and the other hooklike elements, is sold under the trademark Velcro and is more fully described in U.S. Pat. No. 2,717,437. However, any physical arrangement of mating coupling surfaces which when mated by engagement with each other resist the tendency to pull the surfaces apart by forces generally along planes parallel to the contacting surfaces while permitting releasability by pulling the surfaces apart by forces generally perpendicular to the surfaces are suitable. Chemical adhesives, such as adhesive masses, having these properties are also suitable for use as the coupling surfaces in the constrictor of this invention and may be preferable in embodiments of disposable constrictors.

FIGS. 1 and 2 show one preferred embodiment of this invention having the elastic portion of the elongated flexible strip at one end having ring 16 affixed to it through loop 21 formed by the end of the elastic portion being folded back upon itself and fastened by loop fastening means 18. The other end of elastic portion 13 is joined to first coupling surface portion 14 by fastening means 19. The opposite end of first coupling surface portion 14 is fastened to one end of second coupling surface portion 15 by fastening means 20. The fastening means in each instance may be any suitable fastening means such as stitching, heat sealing or any other suitable fastening means which does not restrict the flexibility of the constrictor. While it is preferred for the elastic portion of the constrictor to be at the end of the flexible strip adjacent the ring, the elastic portion may also be located between the coupling surface portions and the ring affixed to one end of one coupling surface portion as shown in FIG. 5. While it is preferred that elastic portion 13 be the only elastic portion of the flexible strip, the backing of first coupling surface portion 14 and second coupling surface portion 15 may be slightly elastic, but not provide the major elasticity as provided by elastic portion 13. Normally, the coupling surfaces will be provided on a flexible backing which is substantially inelastic. As seen in the figures, the coupling surfaces are backed by a very thin sheet of plastic which provides a very lightweight flexible strip.

Ring 16 may be of any suitable shape providing attachment to one end of the elongated flexible strip at one side and allowing threading and free movement for reversal of the flexible strip through the other side of the ring. Generally, it is preferred that the ring be generally rectangular in shape as shown in the figures. The ring may be made of any suitable metallic or synthetic polymeric material.

End tab 17 is generally provided by an area at the end of the flexible strip to which second coupling surface has not been applied, thereby providing an end portion which is always loose and can be used as a lifting tab to lift one coupling surface from the other for adjustment or removal of the constrictor. Also, end tab 17 may be provided by folding the end of the strip having the coupling surface back over itself and heat sealing or fastening the end of the strip to the underlying strip, which, due to the thickness of the coupling surface provides an enlarged end to aid in holding the tab.

FIGS. 3 and 4 show use of the constrictor of one embodiment of this invention around a limb. As seen in those figures, the elongated flexible strip is placed around the limb with its opposite smooth face adjacent the limb, end tab 17 is threaded through ring 16 and the flexible strip reversed upon itself. The constrictor may be controllably tightened to desired force by pulling end tab 17 and when desired force is achieved the constrictor may be retained in that position by pressing the opposing coupling surfaces together. In use, one end of the elongated flexible strip may be threaded through ring 16 before it is applied to the limb and slipped over the end of the limb with one hand and tightened by pulling the loose end to desired tightness. As seen in FIG. 4, the smooth face of the constrictor may be provided with pressure applicator 24 which may be permanently or removably mounted in the desired location. Pressure applicator 24 may be any suitable material such as latex or rubber and is useful to control or reduce bleeding from puncture wounds or needle insertions.

FIG. 5 shows another embodient of the constrictor of this invention wherein elastic portion 13 is located betweed first coupling surface portion 14 and second coupling surface portion 15 with ring 16 affixed to coupling surface portion 14.

Figure 6:
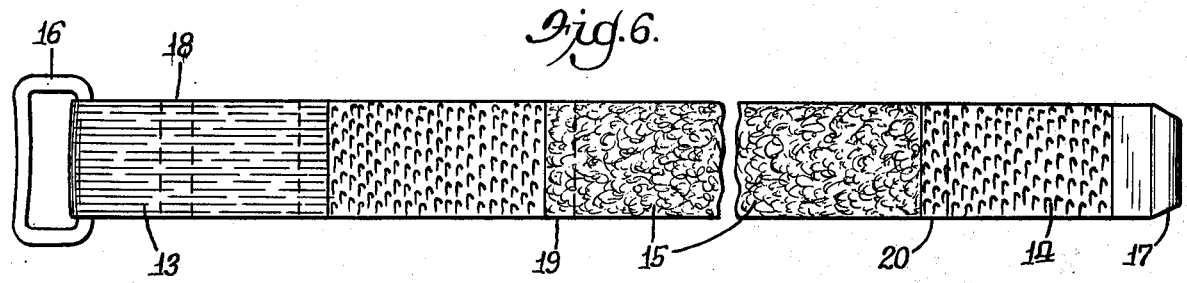
FIG. 6 shows one face of a constrictor according to another embodiment of this invention providing a constrictor having a wide variety of size ranges.

FIG. 6 shows another embodiment of the constrictor of this invention, especially suitable for a wide variety of sizes, wherein a second portion of first coupling surface portion 14 is located adjacent end tab 17. This configuration provides for first coupling surface portion 14 at the end of the elongated strip to couple with second coupling surface portion 15. This provides extremely large size range usability for a single constrictor.

Figure 7:
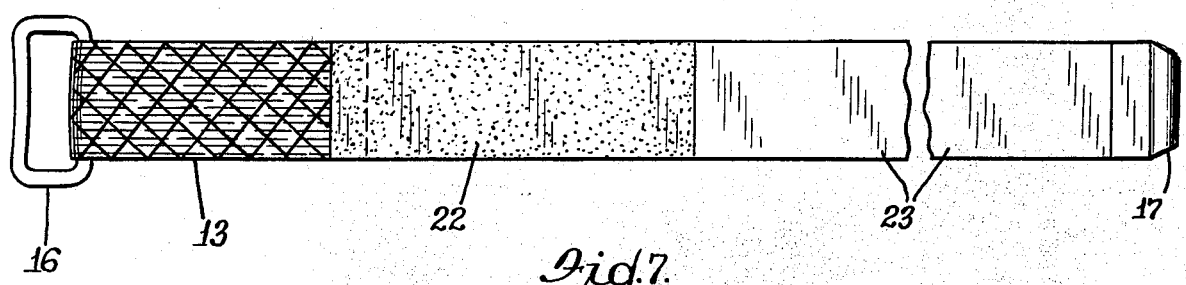
FIG. 7 shows one face of a constrictor according to another embodiment of this invention especially suitable for disposable constrictors.

FIG. 7 shows a constrictor according to another embodiment of this invention which is particularly suitable for disposable units. The constrictor shown in FIG. 7 has the same relationship of components as the constrictor shown in FIG. 1. The coupling surfaces shown in FIG. 7 comprise adhesive first coupling surface portion 22 and smooth second coupling surface portion 23. The adhesive coupling surface may be a suitable adhesive mass as conventionally used for small bandages providing required resistance to sliding motion when in contact with the second coupling surface portion. The second coupling surface portion may be folded over the adhesive coupling surface prior to use or a separate protective strip may be used to prevent undesired adhesion prior to use. The adhesive coupling surface may also be used in the configurations as shown in FIGS. 5 and 6. In FIG. 7, elastic portion 13 is a molded plastic having an embossed design providing elastic properties.

While some of the figures show a constrictor of this invention having Velcro type coupling surfaces with projecting loops as one coupling surface and a multiplicity of curly filament members as the other coupling surface, the relationship of these coupling surfaces is not meant to be restrictive but is shown for illustrative purposes only, the two types of coupling surfaces may be readily interchanged with respect to position.

I have found that a constrictor offering versatility desired for medical uses may be provided wherein about 6 to about 17 percent of the length of the elongated flexible strip is elastic, about 17 to about 28 percent of the length is a first coupling surface and about 55 to about 77 percent of the length is a second coupling surface. Particularly suitable relationships are about 11 percent elastic, about 22 percent first coupling surface and about 67 percent second coupling surface. When the embodiment as shown in FIG. 6 is used, about 10 percent of the length at the end of the second coupling surface is provided as first coupling surface. The actual dimensions are dependent upon the use to which the constrictor is going to be used. I have found that a constrictor offering versatility desired for medical uses on limbs may be provided by a 1 or 2 inch wide flexible strip having about 1 to 3 inches of elastic attached to the ring at one end, the other end of the elastic attached to about 3 to 5 inches of a first coupling surface, the first coupling surface attached at its other end to about 10 to 14 inches or more of a second coupling surface having an end tab of about ⅛ to 1 inch at the loose end. It is readily apparent that the actual dimensions may be enlarged to provide encirclement of the body trunk.

The constrictor of this invention provides an excellent means of providing desired pressure to joints, such as "tennis elbow" and to provide desired pressure to broken ribs and the like, thereby avoiding inelastic bandages and undesired taping. The constrictor of this invention, with its elastic portion, will never completely occlude and therefore will always provide some circulation and will not injure internal vessels. The constrictor of this invention may be used to hold wound dressings, particularly in difficult locations, by encompassing the portion of the body to which the wound dressing is applied without requiring tape or other injurous methods of attachment.

Throughout this disclosure and in the claims, the term "constrictor" has been used in connection with exemplifying this invention with respect to its medical applications. However, the term "constrictor" should not be restricted to medical uses and it is readily apparent the constrictor of this invention may be used to apply a pressure around any object or to hold a multiplicity of objects together and this meaning of the term "constrictor" is meant by use of the term throughout the description and the claims.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A constrictor for medical use comprising; an elongated flexible strip having a ring affixed to one end and an end tab at the other end, said strip consisting of an elastic portion, a first coupling surface portion and a second coupling surface portion on the same face of the strip, said first and second coupling surfaces cooperating upon contact to provide resistance to slidable motion between said surfaces and providing disengagement by separation of the surfaces, said elastic portion being about 6 to 17 percent, said first coupling surface portion about 17 to 28 percent, and said second coupling surface portion about 55 to 77 percent of the length of said elongated flexible strip, said strip being of a length that it will encompass a limb or trunk of a patient, pass through said ring and reverse upon itself such that said first and second coupling surface portions will attach to each other, said constrictor being capable of application and adjustment using one hand by passing said end tab through said ring and pulling said second coupling surface portion back over itself to engage said first coupling surface portion.

2. The constrictor of claim 1 wherein said first coupling surface is comprised of a multiplicity of outwardly projecting loops of filamentary material and said second coupling surface is comprised of a multiplicity of curly filamentary members releasably engagable with said loops.

3. The constrictor of claim 2 wherein said coupling surfaces are comprised of Velcro, one of which comprises projecting loops and the other comprises hook-like elements.

4. The constrictor of claim 2 wherein said ring is affixed to said elastic portion.

5. The constrictor of claim 1 wherein said first coupling surface comprises an adhesive mass and said second coupling surface comprises a surface for mating with said adhesive mass.

6. The constrictor of claim 1 wherein said ring is affixed to said elastic portion.

7. The constrictor of claim 1 wherein said ring is affixed to said first coupling surface portion and said elastic portion is between said first and second coupling surface portions.

8. The constrictor of claim 1 wherein said elastic portion is about 11 percent, said first coupling surface portion is about 22 percent and said second coupling surface portion is about 67 percent of the length of said strip.

9. The constrictor of claim 1 having a pressure applicator affixed to the face of said strip opposite said coupling surface portions to provide controlled pressure to an area in contact with said pressure applicator.

10. The constrictor of claim 1 having a pressure applicator affixed to the face of said strip opposite said first coupling surface portion to provide controlled pressure to an area in contact with said pressure applicator.

* * * * *